United States Patent [19]

Koskan et al.

[11] Patent Number: 5,373,086
[45] Date of Patent: Dec. 13, 1994

[54] POLYASPARTIC ACID HAVING MORE THAN 50% β FORM AND LESS THAT 50% α FORM

[75] Inventors: Larry P. Koskan, Orland Park; Kim C. Low, Alsip; Abdul R. Y. Meah, Justice; Anne M. Atencio, Riverdale, all of Ill.

[73] Assignee: Donlar Corporation, Bedford Park, Ill.

[21] Appl. No.: 186,974

[22] Filed: Jan. 26, 1994

Related U.S. Application Data

[63] Continuation-in-part of Ser. No. 844,506, Mar. 2, 1992, abandoned, which is a continuation-in-part of Ser. No. 671,393, Mar. 19, 1991, Pat. No. 5,152,902.

[51] Int. Cl.$^5$ ............................................. C08G 69/10
[52] U.S. Cl. .................................. 528/328; 525/419; 525/420; 528/499
[58] Field of Search ................ 528/328, 499; 525/419, 525/420

[56] References Cited

U.S. PATENT DOCUMENTS 3,927,204 12/1975 Neri et al. ........................ 528/328
5,152,902 10/1992 Koskan et al. ................... 210/698

Primary Examiner—Morton Foelak
Assistant Examiner—Shelley A. Dodson
Attorney, Agent, or Firm—Olson & Hierl, Ltd.

[57] ABSTRACT

β-Polyaspartic acid having a weight average molecular weight of 1000 to 5000 produced by hydrolysis of anhydropolyaspartic acid exhibits a high degree of calcium carbonate and calcium phosphate inhibition.

4 Claims, 4 Drawing Sheets

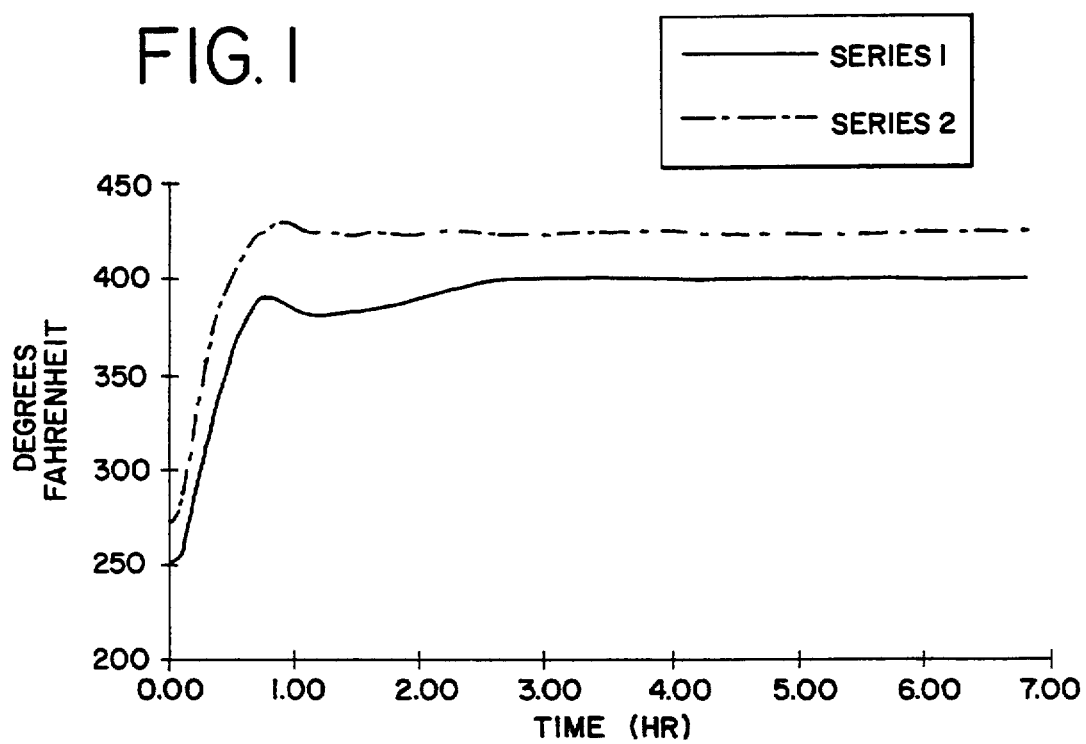
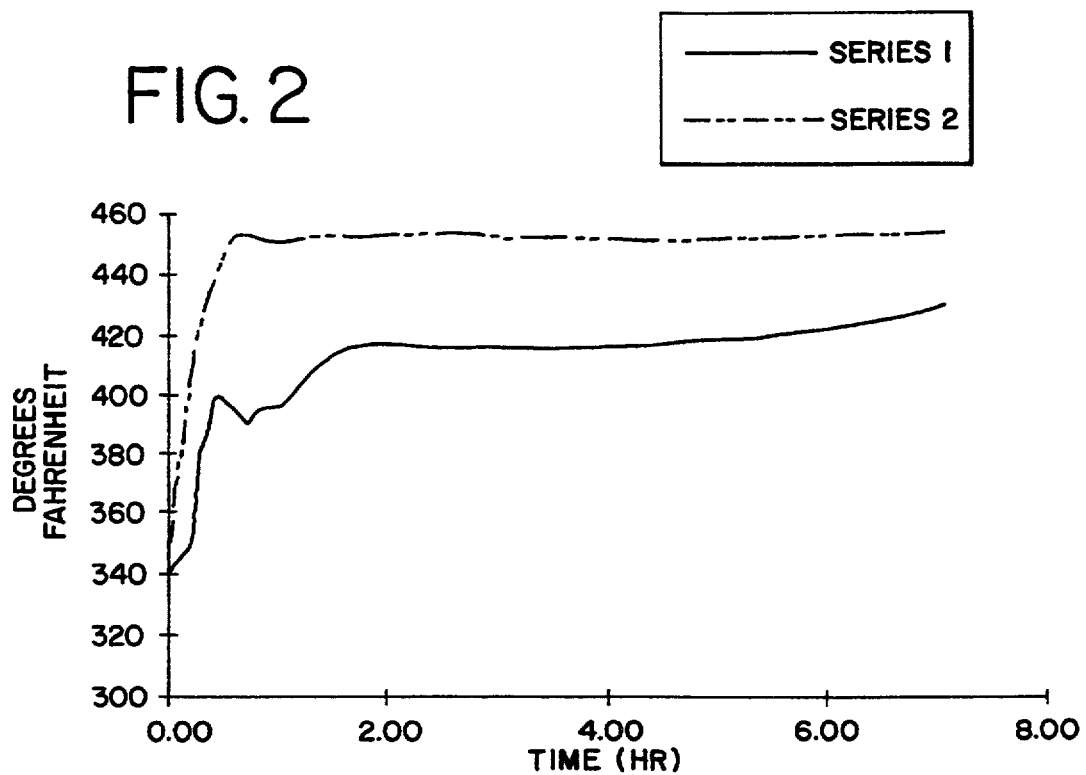

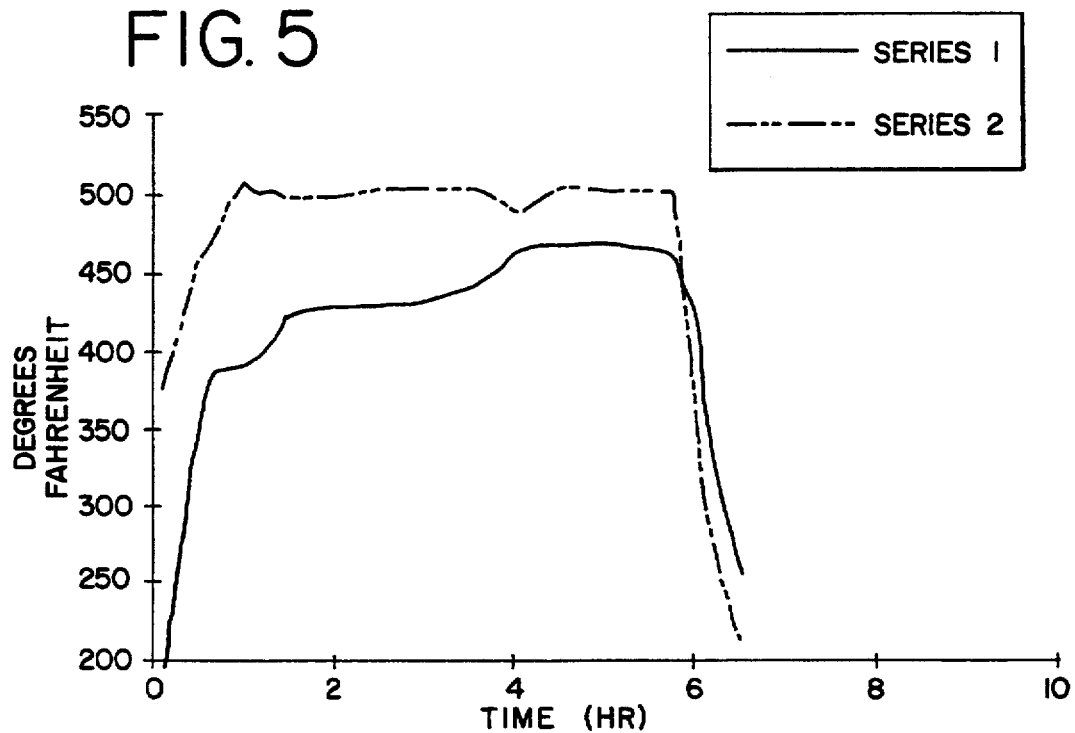
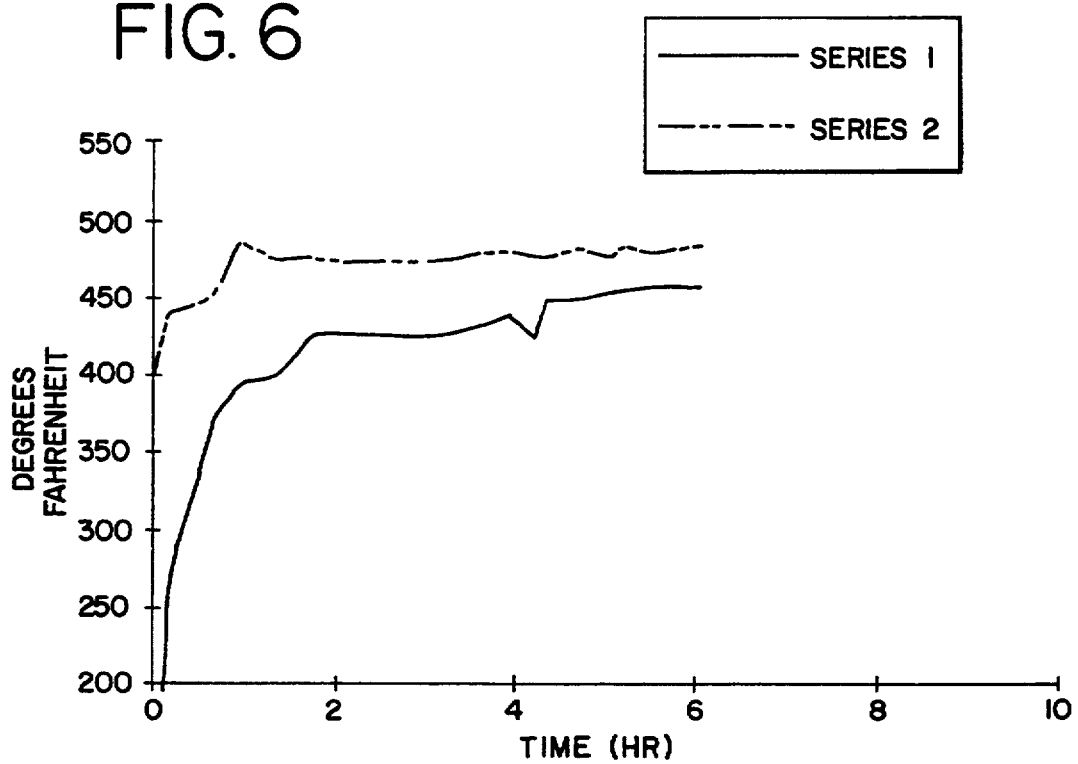

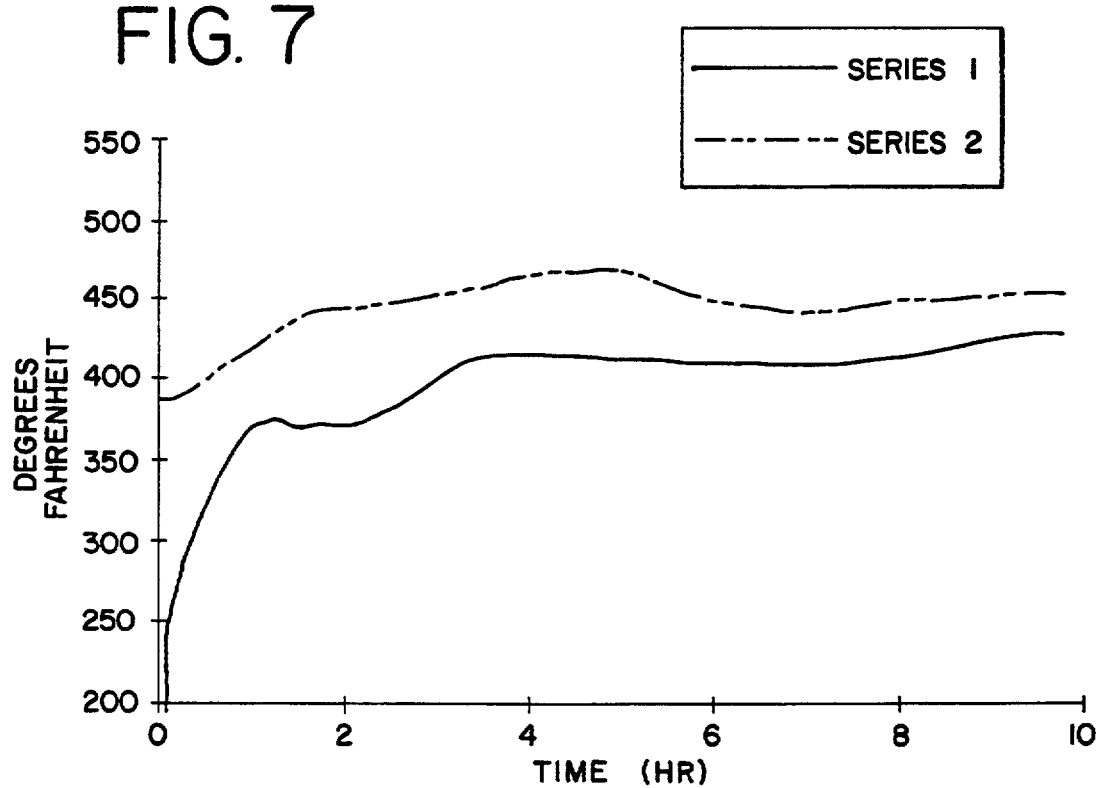

POLYASPARTIC ACID HAVING MORE THAN 50% β FORM AND LESS THAT 50% α FORM

CROSS-REFERENCE TO RELATED APPLICATIONS

This application is a continuation-in-part of copending U.S. application Ser. No. 07/844,506 filed on Mar. 2, 1992 now abandoned which, in turn, is a continuation-in-part of U.S. application Ser. No. 07/671,393, filed on Mar. 19, 1991, now U.S. Pat. No. 5,152,902.

1. Field of the Invention

The present invention relates to a method of using polyaspartic acid to inhibit the precipitation of calcium carbonate and/or calcium phosphate.

2. Background of the Invention

The biodegradability of polyaspartic acids makes them particularly valuable from the point of view of environmental acceptability and waste disposal. After polyaspartic acid has been utilized, it biodegrades to environmentally acceptable end products.

Anhydropolyaspartic acids (i.e. polysuccinimides) are the anhydrous forms of polyaspartic acids.

Thermal condensation of aspartic acid to produce polyaspartic acid is taught by Kokufuta, et al., "Temperature Effect on the Molecular Weight and the Optical Purity of Anhydropolyaspartic Acid Prepared by Thermal Polycondensation", Bulletin of the Chemical Society Of Japan, Vol. 51 (5), 1555-1556 (1978). Kokufuta et al. teach that the molecular weight of the polyaspartic acid produced by this method increases with increased reaction temperature. Moreover, the maximum conversion of the aspartic acid to anhydropolyaspartic acid suggested is no more that 68% using oil bath temperatures of between 325° F. and 425° F.

A more recent work by Little et al., "Corrosion Inhibition By Thermal Polyaspartate" *Surface Reactive Peptides and Polymers*, pp. 263–279, American Chemistry Society Symposium Series 444 (1990), cites Kokufuta et al. According to Little et al., oil bath temperatures of 374° F. were used to produce anhydropolyaspartic acid from powdered aspartic acid over a period of 24 to 96 hours. The results were no better than those reported by Kokufuta et al., however.

Calcium phosphate and calcium carbonate inhibitors are used in a number of applications to prevent precipitation and scale formation. Included among these are cooling water treatment, boiler water treatment, desalination, reverse osmosis, flash evaporators, oil field recovery operations, and for plaque and tartar control.

It is known that polyaspartic acids have utility as calcium carbonate inhibitors. Sikes U.S. Pat. No. 4,534,881 et al. at col 14, Table 4, teaches a calcium carbonate activity test lag phase of 120 minutes for a 0.05 μg/l polyaspartate concentration at 20° C.

It is known that polyaspartic acids inhibit calcium phosphate crystallization, Sikes et al., "Inhibition of Calcium Carbonate and Phosphate Crystallization by Peptides Enriched in Aspartic Acid and Phosphoserine", ACS Symposium Series 444 (1991).

SUMMARY OF THE INVENTION

We have discovered an improved method of inhibiting calcium carbonate or calcium phosphate in aqueous systems. More particularly, we have discovered that a predominantly β-polyaspartic acid in an aqueous system can provide a calcium carbonate activity test lag phase at 0.05 μg/ml generally greater than 190 minutes. More preferably, the lag phase exceeds 210 minutes, and most preferably the lag phase exceeds 270 minutes.

The polyaspartic acid taught by Sikes et al., "Inhibition of Calcium Carbonate and Phosphate Crystallization by Peptides Enriched in Aspartic Acid and Phosphoserine", ACS Symposium Series 444 (1991), is an β-polyaspartic acid. We have discovered that a β-polyaspartic acid has calcium phosphate inhibition characteristics similar to those of polyacrylic acids used for that purpose in cooling water treatment, boiler water treatment, desalination, reverse osmosis, flash evaporators, oil field recovery operation and for plaque and tartar control.

A β-polyaspartic acid (i.e. one having >50% β and >50% α-form), and having an average molecular weight (Mw) within the range of 1000 to 5000 will work. Preferably, the polyaspartic acid is 65%-80% β and 20% to 25%, and has a Mw within the range of 1000 to 5000. More preferably, the polyaspartic acid is approximately 70% to 80% β and 20% to 30% α, and has an Mw within the range of 3000 to 5000. Most preferably, the polyaspartic acid is approximately 70% to 75% β and 25% to 30% α, and has an Mw within the range of 3000 to 5000.

The polyaspartic acid can be produced by the steps of heating powdered L-aspartic acid to at least 370° F. to initiate a condensation reaction, then raising the reaction mixture temperature to at least 420° F., maintaining at least the 420° F. until at least 80% conversion to polysuccinimide has occurred, and hydrolyzing the polysuccinimide.

BRIEF DESCRIPTION OF THE DRAWINGS

In the drawings,

FIG. 1 depicts a temperature versus time reaction curve. Series 2 is the oil temperature. Series 1 is the reaction mixture temperature.

FIG. 2 depicts a temperature versus time reaction curve. Series 2 is the oil temperature. Series 1 is the reaction mixture temperature.

FIG. 5 depicts a temperature versus time reaction curve. Series 2 is the oil temperature. Series 1 is the reaction temperature.

FIG. 6 depicts a temperature versus time reaction curve. Series 2 is the oil temperature. Series 1 is the reaction mixture temperature.

FIG. 7 depicts a temperature versus time reaction curve. Series 2 is the oil temperature. Series 1 is the reaction mixture temperature.

DESCRIPTION OF PREFERRED EMBODIMENTS

Figure 3:
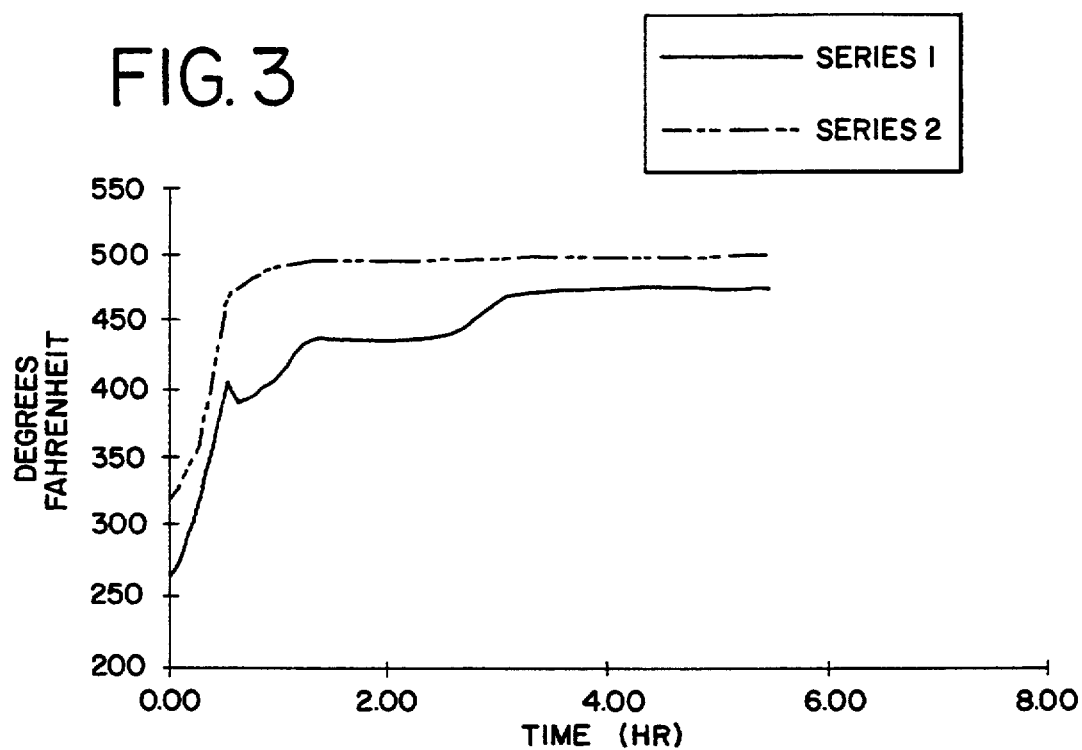
FIG. 3 depicts a temperature versus time reaction curve. Series 2 is the oil temperature. Series 1 is the reaction mixture temperature.

A series of experiments were conducted to thermally polymerize solid phase L-aspartic acid. In each instance, the powdered L-aspartic acid was added to a reaction vessel and heated. Samples were taken throughout the polymerization reaction. Those samples were analyzed for percent conversion to the product, polysuccinimide, and the color and temperature of the samples were noted. The polysuccinimide was then hydrolyzed to produce polyaspartic acid, and activity tests were conducted on the polyaspartic acid.

Each of these, conversion, color, production of polyaspartic acid, and activity are described below.

The following procedure was utilized to determine the percent conversion of the L-aspartic acid to the product, polysuccinimide:

A specific amount of the reaction mixture or product was dissolved in an aliquot of dimethylformamide (DMF). The dissolution was allowed to proceed for 4 to 5 hours until all of the polysuccinimide dissolved in the DMF leaving unreacted L-aspartic acid which was filtered out.

The amount of unreacted L-aspartic acid was determined and conversion was calculated by using the following formula:

$$\% \text{ CONVERSION} = \frac{A - B}{A} * 100\%$$

Where:
A = weight of initial sample
B = weight of residue (unreacted L-aspartic acid)

COLOR

The color of each product sample was noted. The color of L-aspartic acid is white. The samples containing polysuccinimide varied in color according to the temperature of the sample taken from the reaction mixture. From low temperature to high, the colors varied as follows: light pink, to pink, to tannish pink, to tan, to light yellow, to yellow. These colors generally corresponded to the percent conversion of the L-aspartic acid, in the same order with light pink indicating the lowest percent conversion and yellow indicating the highest percent conversion. The pink color has less that 70% conversion. The literature has never reported any other color but pink.

POLYASPARTIC ACID

Polyaspartic acid was produced from polysuccinimide using the following hydrolysis procedure:

A slurry made from a measured amount of polysuccinimide and distilled water. Sodium hydroxide was added dropwise to hydrolyze polysuccinimide to polyaspartic acid. The completion of the hydrolysis was attained at pH 9.5.

Bases other than sodium hydroxide can be used. Suitable bases include ammonium hydroxide, potassium hydroxide, and other alkaline and alkaline earth hydroxides or carbonates.

Generally, base is added to the slurry until the pH has been raised to 9.5, and a clear solution has been formed.

CALCIUM CARBONATE ACTIVITY TEST

Polyaspartic acid was produced from the samples of polysuccinimide. The activity of the polyaspartic acid as an inhibitor for preventing the precipitation of calcium carbonate was determined as described in the test below:

A standard volume of distilled water was pipetted into a beaker. Inhibitor was added after the addition of a calcium chloride solution, but prior to the addition of a solution of sodium bicarbonate. Sodium hydroxide was then added to the solution until there was an apparent and sudden calcium carbonate precipitation evidenced by the cloudiness of the solution.

At this point, the pH dropped, the addition of the sodium hydroxide was stopped, and the pH was recorded. The volume of sodium hydroxide consumed was noted. The pH drop after ten minutes was recorded.

The amount of inhibitor used was adjusted to provide a constant weight of polyaspartic acid in each of the tests.

The activity of the inhibitor was judged by the volume of sodium hydroxide consumed and by the pH drop. The greater the amount of sodium hydroxide needed, the greater the activity of the product as an inhibitor. The smaller the pH drop, the greater the activity of the product as an inhibitor. to The table below provides a summary of the samples tested.

TABLE A

| | Volume of NaOH (ml) | ph drop |
|---|---|---|
| Control | 0.95 | 1.46 |
| Polyaspartic acid (1 ppm) | 1.65 | 1.00 |
| Polyacrylic acid** (1 ppm) | 1.70 | 0.83 |
| Polyaspartic acid (2.5 ppm) | 1.75 | 0.48 |
| Polyacrylic acid** (2.5 ppm) | 1.70 | 0.60 |
| Polyaspartic acid (10 ppm) | 2.40 | 0.30 |
| Polyacrylic acid** (10 ppm) | 2.25 | 0.31 |
| Polyaspartic acid (100 ppm) | 2.65 | 0.02 |
| Polyacrylic acid** (100 ppm) | * | * |

*Precipitation of calcium carbonate occurs at the onset of the test.
**Polyacrylic acid is Rohm & Haas 4500 Mw polyacrylic acid.

CALCIUM CARBONATE NUCLEATION ASSAY

A calcium carbonate nucleation assay was performed at 20° C. as follows:

Inhibitor was added to a mixture containing 200 µl of 1 M calcium chloride dihydrate and 19.4 ml of distilled water. 400 µl of 0.4 M sodium bicarbonate was then added and the pH adjusted to 8.30 with 0.1 N NaOH. The pH of the solution was noted every minute. The higher the lag time (i.e. the lag phase) the better the inhibition effect. The lag times are reported in Table B:

TABLE B

| | 0.2 µg/ml | 0.4 µg/ml |
|---|---|---|
| Control | 2 minutes | 2 minutes |
| Sample A | 7 minutes | 9 minutes |
| Sample B | 6 minutes | 8 minutes |

Sample A is polyaspartic acid obtained from Sigma Chemical Company having a molecular weight of approximately 4900 Mw.
Sample B is polyaspartic acid produced by thermal condensation as taught under the heading "EXPERIMENTS" in this document.

A second series of tests were conducted using the above procedure; however, artificial sea water was substituted for distilled water. The sea water had the following makeup: 500 mM NaCl, 10 mM KCl, 10 mM Ca, and 10 mM dissolved inorganic carbon.

The results are reported in Table C:

TABLE C

| | Conc. | Lag Phase |
|---|---|---|
| 1) Product 1 | 0.05 ppm | 120 minutes |
| 2) Product 2 | 0.05 ppm | 180 minutes |
| 3) Product 3 | 0.05 ppm | 271 minutes |

Product 1 is polyaspartic acid purchased from Sigma Corporation that was considered to be an α-polyaspartic acid.
Product 2 is a thermally prepared polyaspartic acid we believe to be 50% α, 50% β.
Product 3 is a β-polyaspartic acid that has been thermally prepared as described in the Laboratory Experiments 1–4, and Pilot Plant Test Runs 1–3.

CALCIUM PHOSPHATE INHIBITION

A known amount of inhibitor was added to 1M calcium chloride solution. A 1M Na$_2$HPO$_4$ solution was mixed in the resulting slurry. The pH change was recorded with time. The results were as follows:

TABLE D

| Control | | β-Polyaspartic acid | | Polyacrylic acid* | |
|---|---|---|---|---|---|
| Time (min) | pH | Time (min) | pH | Time (min) | pH |
| 0 | 7.41 | 0 | 7.41 | 0 | 7.40 |
| 5 | 7.40 | 5 | 7.41 | 5 | 7.40 |
| 10 | 7.38 | 10 | 7.41 | 10 | 7.39 |
| 15 | 7.36 | 15 | 7.40 | 15 | 7.39 |
| 20 | 7.33 | 20 | 7.39 | 20 | 7.37 |
| 25 | 7.23 | 25 | 7.38 | 25 | 7.35 |
| 30 | 6.77 | 30 | 7.35 | 30 | 7.33 |
| 35 | 6.71 | 35 | 7.33 | 35 | 7.17 |
| 40 | 6.71 | 40 | 7.21 | 40 | 7.01 |
|  |  | 45 | 6.91 | 45 | 6.96 |
|  |  | 50 | 6.80 | 50 | 6.89 |
|  |  | 55 | 6.77 | 55 | 6.83 |
|  |  | 60 | 6.76 | 60 | 6.80 |

*Rohm & Haas 4500 Mw polyacrylic acid

This data shows that the β-polyaspartic acid of this invention and polyacrylic acid have comparable calcium phosphate inhibition characteristics.

MOLECULAR WEIGHT DETERMINATION

Gel permeation chromatography was utilized to determine the molecular weights of the polyaspartic acid produced. The molecular weight determinations were made on the polysuccinimide that was hydrolyzed using the hydrolysis procedure described herein.

Rohm & Haas 2000 Mw polyacrylic acid and Rohm & Haas 4500 Mw polyacrylic acid were utilized as standards. The molecular weights provided for the polyaspartic acid produced according to this invention are based on these standards unless otherwise noted, and are reported as weight average molecular weights (Mw). This is because molecular weights based on gel permeation chromatography can vary with the standards utilized.

It was found that the molecular weight for the polyaspartic acid produced fell within the range of 1000 Mw to 5000 Mw, regardless of percent conversion.

β COMPOSITION

The polyaspartic acid produced is a copolymer containing two forms of L-aspartic acid derivatives. The α form is a 2-carboxymethylacetamide derivative. The β form is a 3-carboxypropionamide derivative.

The polyaspartic acid prepared according to the procedures described in Laboratory Experiments 1-4 and Pilot Plant Test Runs 1-3 under the heading "EXPERIMENTS" can be termed β-polyaspartic acid, since NMR studies show it contains greater than 50% 2-carboxypropionamide derivatives and less than 50% 2-carboxymethylacetamide derivatives.

The NMR analysis was conducted on two different product samples. One sample had 70% β form; the other had 75% β form. It is believed that by varying hydrolysis condition, greater or lesser percentages of β can be achieved.

Thus, the polyaspartic acids exemplifying this invention, have greater than 50% β, less that 50% α form, and a weight average molecular weight within the range of 1000 to 5000. Preferably, the polyaspartic acids produced by this method are approximately 65% to 80% β and 20% to 35% α polyaspartic acid, and have a weight average molecular weight within the range of 1000 to 5000. More preferably, they are 70% to 80% β and most preferably they are 70% to 75% β with weight average molecular weights within the range of 3000 to 5000.

POLYASPARTIC ACID PRODUCT

We have discovered how to produce a much higher percent conversion polyaspartic acid than has been taught or suggested by the prior art. Moreover, contrary to the teachings of the prior art, the molecular weight of the polyaspartic acid produced by our method does not increase with the reaction temperature.

We have discovered that the thermal condensation of powdered L-aspartic acid to produce polysuccinimide in high yields optimally occurs above the initiation temperature of about 370° F. and preferably occurs above 420° F., and most preferably occurs above 440° F.

A reactant temperature less than 370° F. may produce polysuccinimide over a period of many hours. Theoretical yields will be low; the conversion of the L-aspartic acid to polysuccinimide will be less than 70% and will require a period of many days.

As the reactant temperature increases above 370° F., the percent conversion increases to greater than 90% and the reaction times become greatly reduced.

The thermal condensation of L-aspartic acid to polysuccinimide according the method of our invention produces a characteristically shaped "temperature vs. time" reaction curve. The curve is characterized by an initial, rapid rise in reactant temperature, followed by an endotherm signally the beginning of the reaction. Immediately following the onset of the endotherm there is evaporative cooling, followed first by a temperature rise, and then by a second endotherm, which is followed by an evaporative cooling plateau. The temperature then rises to a plateau. That plateau is at a constant temperature. The reaction has gone to at least 95% conversion at the temperature midway between the final plateau and the time the temperature begins to rise to that plateau.

Polyaspartic acid is produced from the polysuccinimide by base hydrolysis.

The polyaspartic acid produced has a weight average molecular weight of 1000 to 5000. This molecular weight range is uniform regardless of the percent conversion.

The percent conversion of the L-aspartic acid to the polysuccinimide can be increased in reduced time periods by increasing the temperatures used.

Where the thermal fluid used to heat the L-aspartic acid is brought to 500° F. in a reasonable time period, at least 90% conversion can be effected within 4 hours.

Where the thermal fluid used to heat the L-aspartic acid is brought to a maintenance temperature of at least 550° F. within a reasonable time period, at least 90% conversion can be effected within 2 hours.

Continuous and batch processes can be used. Some process examples include fluidized bed; stirred reactor; and indirectly, heated rotary driers.

DEFINITIONS

The term polyaspartic acid used herein also includes salts of polyaspartic acid. Counterions for polyaspartate include, but are not limited to, the alkaline and alkaline earth cations, some examples of which are Na+, K+, Mg++, and Li+, Ca++, Zn++. Ba++, Co++, Fe++, Fe+++, and NH+4.

Polysuccinimide is the imide form of polyaspartic acid and is also known as anhydropolyaspartic acid.

Conversion is defined to be the degree to which L-aspartic acid has formed polysuccinimide by thermal condensation.

Equilibrium temperature is defined to be the temperature of the product upon completion of the reaction.

EXPERIMENTS

Reported below are examples of the production of polysuccinimide and polyaspartic acid.

Laboratory Experiment 1

A "time vs. temperature" plot of the following reaction is depicted in FIG. 1.

A 500 ml covered, stainless steel, beaker charged with 400 grams of powdered L-aspartic acid was placed in an oil bath. The oil bath was quickly heated to a 425° F. maintenance temperature. The sample was stirred through the experiment.

At 40 minutes, the reaction began when the first endotherm was reached. The first endotherm of the reaction mixture peaked at 390° F. at an oil temperature of 425° F. which was the maintenance temperature.

Evaporative cooling immediately followed this first endotherm. Water loss was evidenced by the evolution of steam. The reaction mixture temperature dropped to a low of 360° F. during this period.

Following the temperature drop, the reaction mixture began to heat up. At about 2.8 hours, the reaction mixture attained a plateau temperature of 400° F. At the end of about 6.9 hours, 42 percent conversion had been attained. Steam coming from the system evidenced water loss throughout the entire endothermic reaction. Evaporative cooling still continued to take place. The experiment was concluded after the seven hour experiment.

Table 1 below provides data developed during this experiment. Samples were taken at the times indicated and analyzed for percent conversion to polysuccinimide.

The relative activity of polyaspartic acid produced from the product polysuccinimide was determined by the calcium carbonate activity test described above. Activity is reported in terms of pH drop (δ pH) and milliliters (mls) of sodium hydroxide, as described in the activity test.

The color of the reaction mixture is provided. Color was observed to vary with product temperature.

TABLE 1

| POLYMERIZATION | | | | ACTIVITY TEST | | |
|---|---|---|---|---|---|---|
| Time hr | Product °F. | Oil °F. | Conv % | NaOH ml | δpH | Color |
| 0.0 | 250 | 270 | 0 | 0.95 | 1.47 | LP |
| 1.0 | 386 | 430 | 5 | — | — | LP |
| 1.7 | 385 | 425 | 13 | 1.75 | 0.56 | P |
| 3.4 | 401 | 425 | 26 | 1.75 | 0.56 | P |
| 5.0 | 400 | 424 | 27 | 1.75 | 0.56 | P |
| 6.9 | 400 | 425 | 42 | 1.80 | 0.57 | P |

The following definitions apply through out this writing: LP = Light Pink; LY = Light Yellow; P = Pink; T = Tan; W = White; Y = Yellow; Conv = Conversion; δpH = activity test pH drop; hr = hours

Laboratory Experiment 2

A "time vs. temperature" plot of the following reaction is depicted in FIG. 2.

A 500 ml covered, stainless steel, beaker charged with 400 grams of powdered, L-aspartic acid was placed in an oil bath. The oil bath was quickly heated to a 450° F. maintenance temperature. The sample was stirred throughout the experiment.

At 30 minutes, the reaction began when the first endotherm was reached. The first endotherm of the reaction mixture peaked at 395° F. at an oil temperature of 439 ° F.

Evaporative cooling immediately followed this first endotherm. Water loss was evidenced by the evolution of steam. The reaction mixture temperature dropped to a low of 390° F. during this period and the oil temperature rose to the 450° F. maintenance temperature.

Following the temperature drop, the reaction mixture began to heat up. At about 1.7 hours, a second endotherm occurred. At this endotherm, the reaction mixture temperature was 420° F. and the oil temperature was 450° F. Steam coming from the system evidenced water loss.

Evaporative cooling continued to take place until the conclusion of the second endotherm. water loss was evidenced by the evolution of steam. At the conclusion of this period, the reaction mixture was then heated up and maintained at an equilibrium temperature of 434° F.

Table 2 below provides data developed during this experiment. Samples were taken at the times indicated and analyzed for percent conversion to polysuccinimide.

The relative activity of polyaspartic acid produced from the product polysuccinimide was determined by the calcium carbonate activity test described above. Activity is reported in terms of pH drop (δ pH) and milliliters (mls) of sodium hydroxide, as described in the activity test.

The color of the reaction mixture is provided. Color was observed to vary with product temperature.

TABLE 2

| POLYMERIZATION | | | | ACTIVITY TEST | | |
|---|---|---|---|---|---|---|
| Time hr | Product °F. | Oil °F. | Conv % | NaOH ml | δpH | Color |
| 0.0 | 340 | 345 | 0 | 0.95 | 1.47 | W |
| 0.5 | 400 | 440 | 22 | — | — | LP |
| 1.1 | 396 | 451 | 23 | 1.75 | 0.59 | LP |
| 1.7 | 422 | 457 | 32 | 1.80 | 0.57 | P |
| 4.2 | 416 | 451 | 58 | 1.81 | 0.61 | P |
| 5.5 | 420 | 452 | 81 | 1.80 | 0.63 | T |
| 7.1 | 430 | 454 | 97 | 1.75 | 0.69 | T |

Laboratory Experiment 3

A "time vs. temperature" plot of the following reaction is depicted in FIG. 3.

A 500 ml covered, stainless steel, beaker charged with 400 grams of powdered, L-aspartic acid was placed in an oil bath. The oil bath was quickly heated to a 500° F. maintenance temperature. The reaction mixture was stirred throughout the experiment.

At 30 minutes, the reaction began when the first endotherm was reached. The first endotherm of the reaction mixture peaked at 405° F. at an oil temperature of 465° F.

Evaporative cooling immediately followed the first endotherm. Water loss was evidenced by the evolution of steam. The reaction mixture temperature dropped to a low of 390° F. during this period, and the oil temperature rose to 490= F.

At 1.25 hours, a second endotherm occurred. At this second endotherm, the reaction mixture temperature was 438° F. and the oil temperature was 495° F.

Evaporative cooling continued to take place until the conclusion of the second endotherm. Water loss was evidenced by the evolution of steam. The reaction mixture temperature dropped to a low of 432° F. during this period and the oil temperature rose to 499° F.

A diminution in evaporative cooling was evidenced by a steady rise in reaction mixture temperature between approximately 2.65 hours and about 3.2 hours. At about 3.2 hours a temperature plateau was attained. No further increase in conversion was noted beyond that point.

Table 3 below provides data developed during this experiment. Samples were taken at the times indicated and analyzed for percent conversion to polysuccinimide.

The relative activity of polyaspartic acid produced from the product polysuccinimide was determined by the calcium carbonate activity test described above Activity is reported in terms of pH drop (δ pH) and milliliters (mls) of sodium hydroxide, as described in the activity test.

The color of the reaction mixture is provided. Color was observed to vary with product temperature.

TABLE 3

TABLE 3

| | POLYMERIZATION | | | ACTIVITY TEST | | |
|---|---|---|---|---|---|---|
| Time hr | Product °F. | Oil °F. | Conv % | NaOH ml | δpH | Color |
| 0.0 | 256 | 316 | 0 | 0.95 | 1.47 | W |
| 0.5 | 406 | 464 | 7 | — | — | LP |
| 1.3 | 437 | 496 | 43 | 1.80 | 0.56 | P |
| 2.3 | 438 | 497 | 81 | 1.80 | 0.56 | P |
| 3.1 | 470 | 499 | 90 | 1.80 | 0.67 | TP |
| 3.8 | 476 | 500 | 95 | 1.80 | 0.63 | TP |
| 6.0 | 476 | 502 | 98 | 1.80 | 0.63 | LY |

Laboratory Experiment 4

Figure 4:
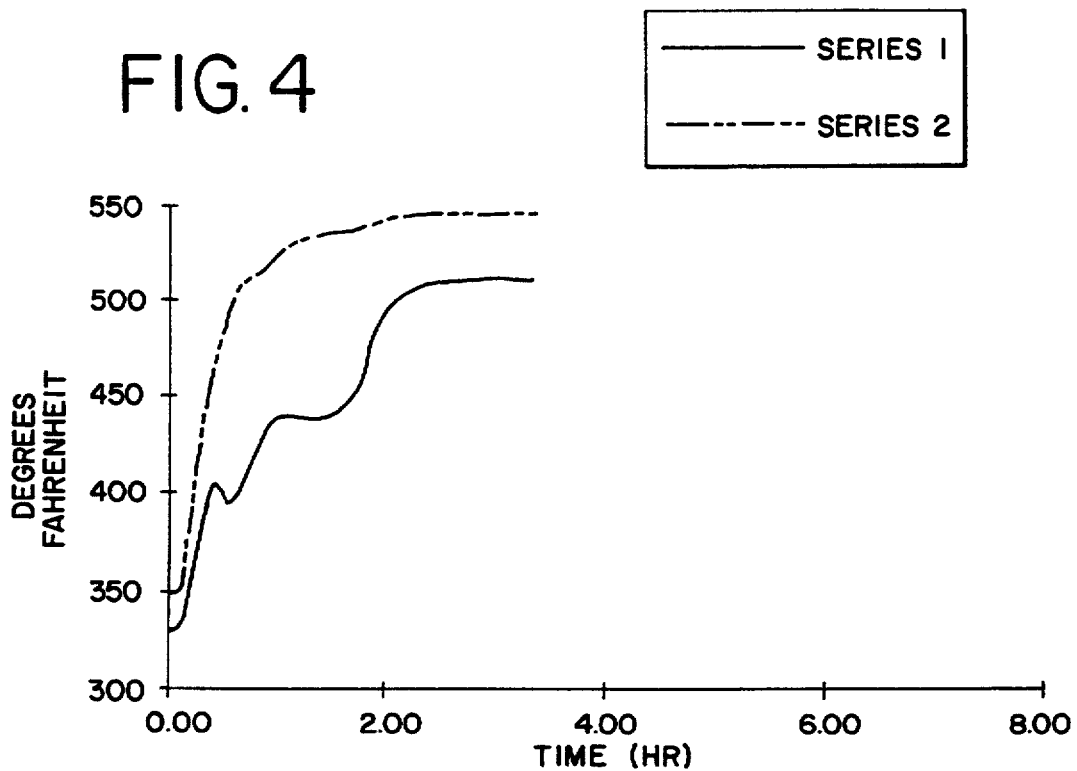
FIG. 4 depicts a temperature versus time reaction curve. Series 2 is the oil temperature. Series 1 is the reaction temperature.

A "time vs. temperature" plot of the following reaction is depicted in FIG. 4.

A 500 ml covered, stainless steel, beaker charged with 400 grams of powdered, L-aspartic acid was placed in an oil bath. The oil bath was quickly heated to a 550° F. maintenance temperature. The sample was stirred throughout the experiment.

At 24 minutes, the reaction began when the first endotherm was reached. The first endotherm of the reaction mixture peaked at 410° F. at an oil temperature of 470° F.

Evaporative cooling immediately followed the first endotherm. Water loss was evidenced by the evolution of steam. The reaction mixture temperature dropped to a low of 395° F. during this period.

A second endotherm occurred at 1 hour at a reaction mixture temperature of 442° F.

Evaporative cooling continued to take place until the conclusion of the second endotherm. The reaction mixture temperature dropped to a low of 440° F. during this period.

A diminution in evaporative cooling was evidence by a steady rise in reaction mixture temperature between approximately 1.5 hours and about 2.1 hours. At about 2.1 hours a temperature plateau was attained. No further increase in percent conversion was noted beyond about 2 hours.

Table 4 below provides data developed during this experiment. Samples were taken at the times indicated and analyzed for percent conversion to polysuccinimide.

The relative activity of polyaspartic acid produced from the product polysuccinimide was determined by the calcium carbonate activity test described above. Activity is reported in terms of pH drop (δ pH) and milliliters (mls) of sodium hydroxide, as described in the activity test.

The color of the reaction mixture is provided. Color was observed to vary with product temperature.

TABLE 4

| | POLYMERIZATION | | | ACTIVITY TEST | | |
|---|---|---|---|---|---|---|
| Time hr | Product °F. | Oil °F. | Conv % | NaOH ml | δpH | Color |
| 0.0 | 330 | 348 | 0 | 0.95 | 1.47 | W |
| 0.5 | 405 | 470 | 11 | — | — | LP |
| 1.0 | 436 | 520 | 36 | 1.80 | 0.60 | LP |
| 1.4 | 439 | 536 | 66 | 1.80 | 0.67 | P |
| 1.8 | 462 | 540 | 92 | 1.80 | 0.58 | TP |
| 2.0 | 495 | 544 | 94 | 1.75 | 0.64 | TP |
| 2.4 | 510 | 547 | 96 | 1.75 | 0.58 | LY |
| 3.4 | 512 | 548 | 98 | 1.80 | 0.63 | Y |

Production scale product runs were conducted as follows:

Pilot Plant Test Run #1

A "time vs. temperature" plot of the following reaction is depicted in FIG. 5.

A DVT-130 drier, mixer manufactured by the Littleford Brothers, Inc., of Florence, Ky. was used. The jacketed drier utilizes a thermal fluid (hereinafter called "oil"), a plough blade impeller, a stack open to the atmosphere; and has a heat transfer area of 10 ft$^2$. The reactor's oil reservoir was preheated to 550° F.

The reactor was charged with 110.4 lb of powdered, L-aspartic acid. Hot oil began to flow through the jacket, and the impeller speed was set at 155 rpm. Both the product and oil temperatures rose steadily. At a product temperature of 390° F., there was a sudden, endothermic reaction which caused the product temperature to drop (see FIG. 5). Water loss was evidenced by the evolution of steam. A sample taken revealed the powder had changed from white to pink. Three percent of the material was converted to polysuccinimide.

Thereafter, product temperature began to rise steadily until it reached a plateau at 428° F. which continued for an hour. Throughout this whole reaction, steam evolved, and the conversion increased in a linear fashion. At the end of the hour, the product temperature rose to 447°F. at which time the reaction underwent a second endotherm. Immediately after this endotherm, steam ceased to evolve. Shortly after this point, the reaction was at least 88% complete. Following the second endotherm, the product slowly changed from a pink to a yellow color. The final conversion was measured at 97%.

Table 5 below provides data developed during this experiment. Samples were taken at the times indicated and analyzed for percent conversion to polysuccinimide.

TABLE 5

| | POLYMERIZATION | | |
|---|---|---|---|
| Time hr | Product °F. | Oil °F. | Conv % |
| 0.0 | 70 | 375 | 0 |
| 0.8 | 390 | 394 | 3 |
| 1.1 | 396 | 504 | 15 |
| 1.5 | 423 | 501 | 24 |
| 2.0 | 430 | 500 | 41 |
| 2.6 | 430 | 506 | 61 |
| 3.6 | 444 | 505 | 84 |
| 4.5 | 471 | 508 | 88 |
| 5.8 | 466 | 506 | 97 |

Pilot Plant Test Run #2

A "time vs. temperature", plot of the following reaction is depicted in FIG. 6.

A Littleford DVT-130 drier, mixer with a heat transfer area of 10 ft$^2$, was charged with 110.4 lb of powdered, L-aspartic acid, and the oil reservoir was preheated to 525° F.

At the start up, hot oil began to flow through the jacket, and the impeller speed was set at 155 rpm. Both the product and oil temperature rose steadily. The product temperature rose to 393° F. whereupon a sudden, endothermic reaction caused the product temperature to drop (see FIG. 6) and steam began to evolve. A sample taken revealed that the powder had changed from white to pink. Four percent of the material was converted to polysuccinimide. Thereafter, product temperature began to rise steadily until it reached a plateau at 427° F. which continued for one and a half hours. Throughout this whole reaction, steam was evolved, and the conversion increased in a linear fashion. At the end of this time, the product temperature rose to 444° F. until the reaction underwent a second endotherm. Immediately after this second endotherm steam ceased to evolve. Shortly after this point, the reaction was at least 94% complete. Following the second endotherm, the product slowly changed from a pink to a yellow color. The final conversion was measured at 98%.

Table 6 below provides data developed during this experiment. Samples were taken at the time indicated and analyzed for percent conversion to polysuccinimide.

TABLE 6

| | POLYMERIZATION | | |
|---|---|---|---|
| Time hr | Product °F. | Oil °F. | Conv % |
| 0.0 | 70 | 400 | 0 |
| 1.0 | 393 | 488 | 5 |
| 1.3 | 400 | 476 | 18 |
| 2.0 | 428 | 475 | 20 |
| 3.9 | 441 | 480 | 66 |
| 4.4 | 450 | 477 | 85 |
| 5.1 | 456 | 476 | 94 |
| 6.1 | 457 | 484 | 98 |

Pilot Plant Test Run #3

A "time vs. temperature" plot of the following reaction is depicted in FIG. 7.

A "B" blender, manufactured by J. H. Day of Cincinnati, Ohio was charged with 110.4 lb of powdered, L-aspartic acid. The unit was a trough-shaped blender with a plough-bladed impeller and a heat transfer area of approximately 8 ft$^2$. The reactor was wrapped in fiberglass insulation because the oil heater was undersized. The reactor also had a large funnel in a top port open to the atmosphere. The oil reservoir was preheated to 500° F. At the start up, hot oil began to flow through the jacket, and the impeller began to rotate at 74 rpm. Both the product and oil temperatures rose steadily. The product temperature rose to 377° F. whereupon a sudden, endothermic reaction caused the product temperature to drop (see FIG. 7) and steam began to evolve. A sample taken revealed that the powder had changed from white to pink. Thirteen percent of the material was converted to polysuccinimide. Thereafter, product temperature began to rise steadily until it reached a plateau at 416° F. which continued for about 3.8 hours. Throughout this whole reaction, steam was evolved, and the conversion increased in a linear fashion. Due to the heater being undersized, it took a longer time for the product temperature to rise. At the end of this time, the product temperature rose to 435° F. The reaction was at least 88% complete. Due to time limitations, the reaction was stopped when the product temperature reached the plateau. At this point, the final conversion was measured at 90%.

Table 7 below provides data developed during this experiment. Samples were taken at the times indicated and analyzed for percent conversion to polysuccinimide.

TABLE 7

| | POLYMERIZATION | | |
|---|---|---|---|
| Time hr | Product °F. | Oil °F. | Conv % |
| 0.0 | 55 | 390 | 0 |
| 1.0 | 370 | 420 | 0 |
| 2.3 | 377 | 448 | 13 |
| 3.0 | 403 | 455 | 21 |
| 3.5 | 416 | 460 | 26 |
| 4.0 | 417 | 469 | 32 |
| 4.5 | 416 | 471 | 38 |
| 5.0 | 416 | 472 | 45 |
| 5.5 | 415 | 460 | 52 |
| 6.8 | 413 | 446 | 64 |
| 7.3 | 414 | 448 | 70 |
| 7.8 | 418 | 451 | 74 |
| 8.3 | 422 | 455 | 81 |
| 9.3 | 433 | 460 | 88 |
| 9.8 | 435 | 460 | 90 |

The experiments show that degree of conversion of L-aspartic acid and the time required for conversion is related to the temperature of the reaction mixture.

The higher the temperature of the thermal fluid used to heat the reaction mixture, the higher the degree of polymerization and the faster the rate of conversion.

Because of normal heat losses, the temperature of the thermal fluid will always be higher than the temperature of the reaction mixture. It is known that increasing the temperature of the thermal fluid will increase the driving force of a reaction. Assuming that the thermal fluid temperature will be raised to its maintenance temperature in a reasonably short period of time, we have found that generally the following has held true:

Where the oil maintenance temperature was 425° F., at the end of 5 days only 60% conversion was achieved. The equilibrium temperature of the reaction mixture appeared to be 400° F.

Where the oil maintenance temperature was 450° F., 90% conversion took place within 7 hours. The equilibrium temperature of the reaction mixture is not known.

Where the oil maintenance temperature was 500° F., 90% conversion took place within 4 hours. The equilibrium temperature of the reaction mixture was 477° F.

Where the oil maintenance temperature was 550° F., 90% conversion took place within 2 hours. The equilibrium temperature of the reaction mixture was 510° F.

The difference between the maintenance temperature and the reaction temperatures provides the driving force. Different means for providing the thermal energy can result in different driving forces. Thus, although the relations derived here are qualitatively valid, there may be some quantitative differences found in different systems. Different thermal resistances will result in a shift in temperature and/or time requirements.

The systems tested here tend to have high thermal resistance. For systems with less thermal resistance, lower source temperatures will suffice to provide equivalent results.

The data indicates that continuous as well as batch processes can be used. The relationships we have just discussed are equally valid for both. Based on the data presented here, a number of different reactors can be used. Examples of these include, but are not limited to a heated rotary drier; a stirred reactor; a fluidized bed and the like. The reaction can occur at ambient pressure or under a vacuum. The reaction can occur in air or a variety of atmospheres, inert or otherwise.

As a further example, an indirectly heated rotary drier having the same resident time as, for example, the DVT 130, would provide similar results under the same operating conditions.

We claim:

1. A polyaspartic acid comprising more than 50% $\beta$-form and less than 50% $\alpha$-form and having a weight average molecular weight within the range of 1000 to 5000.

2. The polyaspartic acid of claim 1, wherein the polyaspartic acid is 65% to 80% $\beta$ and 20% to 35% $\beta$.

3. The polyaspartic acid of claim 1, wherein the polyaspartic acid is 70% to 80% $\beta$ and 20% to 30% $\alpha$ and has a weight average molecular weight within the range of 3000 to 5000.

4. The polyaspartic acid of claim 1, wherein the polyaspartic acid is 70% to 75% $\beta$ and 25% to 30% $\alpha$ and has a weight average molecular weight within the range of 3000 to 5000.

* * * * *

UNITED STATES PATENT AND TRADEMARK OFFICE
CERTIFICATE OF CORRECTION

PATENT NO. : 5,373,086
DATED : December 13, 1994
INVENTOR(S) : Larry P. Koskan et al.

It is certified that error appears in the above-indentified patent and that said Letters Patent is hereby corrected as shown below:

Col. 1, line 54, before "et al." insert – Sikes –.

Col. 2, line 8, "$\beta$-polyaspartic" should be – $\alpha$-polyaspartic –.

Col. 2, line 19, after "25%" insert – $\alpha$ –.

Col. 4, line 12, after "inhibitor." delete "to".

Col. 6, line 3, after "75% $\beta$" insert a comma (,).

Col. 8, line 26, "water" should be – Water –.

Col. 14, line 14, "35% $\beta$" should be – 35% $\alpha$ –.

Col. 14, line 16, after "30% $\alpha$" insert a comma (,).

Signed and Sealed this

Thirty-first Day of October 1995

Attest:

BRUCE LEHMAN

*Attesting Officer*  *Commissioner of Patents and Trademarks*